US007074419B2

(12) United States Patent
Dietz et al.

(10) Patent No.: US 7,074,419 B2
(45) Date of Patent: Jul. 11, 2006

(54) COSMETIC AND PHARMACEUTICAL OIL-IN-WATER EMULSIONS

(75) Inventors: Thomas Dietz, Essen (DE); Peter Hameyer, Essen (DE); Klaus Jenni, Witten (DE)

(73) Assignee: Goldschmidt GmbH, Essen (DE)

( * ) Notice: Subject to any disclaimer, the term of this patent is extended or adjusted under 35 U.S.C. 154(b) by 0 days.

(21) Appl. No.: 09/777,544

(22) Filed: Feb. 6, 2001

(65) Prior Publication Data

US 2001/0046507 A1 Nov. 29, 2001

(30) Foreign Application Priority Data

Feb. 19, 2000 (DE) ................................ 100 07 649

(51) Int. Cl.
*A61K 6/00* (2006.01)
*A61K 8/00* (2006.01)
*A61K 8/72* (2006.01)

(52) U.S. Cl. ................. 424/401; 424/70.11; 424/70.12

(58) Field of Classification Search ................ 424/401, 424/70.11, 70.12
See application file for complete search history.

(56) References Cited

U.S. PATENT DOCUMENTS 5,965,115 A * 10/1999 Bolich et al. ............... 424/401
6,277,893 B1 * 8/2001 Babenko ...................... 516/67
6,488,780 B1 * 12/2002 Cauwet-Martin ............ 134/42

FOREIGN PATENT DOCUMENTS

DE 37 40 186 A1 1/1989
DE 39 38 140 A1 8/1991
DE 40 09 347 A1 9/1991
DE 42 04 321 A1 8/1993
DE 42 41 799 C1 1/1994
DE 42 29 707 A1 3/1994
DE 42 29 737 A1 3/1994

(Continued)

OTHER PUBLICATIONS

Stedman's Medical dictionary 27th Edition, "emulsion" 2000.*
German Publication 1 165 574, Oct 1, 1964.
O'Lenick, Jr., et al., "Three-Dimensional HLB", Cosmetics and Toiletries Magazine, vol. 111, Oct. 1996, pp. 37-44.
"List of Colours According to Colour Index Number", DFG-Namen, pp. 80-107.

(Continued)

*Primary Examiner*—Shengjun Wang
(74) *Attorney, Agent, or Firm*—Scully, Scott, Murphy & Presser, P.C.

(57) ABSTRACT

The present invention relates to the use of a polyether-modified polysiloxanes of a defined structure for the preparation of cosmetic and pharmaceutical oil-in-water emulsions, and to oil-in-water emulsions which comprise said polysiloxanes.

19 Claims, 2 Drawing Sheets

FOREIGN PATENT DOCUMENTS

| | | |
|---|---|---|
| DE | 42 37 081 A1 | 5/1994 |
| DE | 42 37 081 C2 | 5/1994 |
| DE | 43 09 372 A1 | 9/1994 |
| DE | 43 24 219 A1 | 1/1995 |
| DE | 198 55 934 A1 | 6/2000 |
| EP | 0 154 837 A2 | 9/1985 |
| EP | 0 279 319 A2 | 8/1988 |
| EP | 0 516 547 A1 | 12/1992 |
| EP | 0 627 259 A2 | 12/1994 |

OTHER PUBLICATIONS

William C. Griffin, "Classification of Surface-Active Agents by "HLB"", Journal of the Society of Cosmetic Chemists, pp. 311-326.

* cited by examiner

COSMETIC AND PHARMACEUTICAL OIL-IN-WATER EMULSIONS

This application claims foreign priority of Germany 10007649.1, filed Feb. 19, 2000.

FIELD OF THE INVENTION

The present invention relates to the use of polyether-modified polysiloxanes of a defined structure for the preparation of cosmetic and pharmaceutical oil-in-water emulsions, and to oil-in-water emulsions which comprise such polyether-modified polysiloxanes.

BACKGROUND OF THE INVENTION

The majority of cosmetic and pharmaceutical emulsions are of the oil-in-water type, i.e., the oil phase ("disperse phase") is very finely distributed in the form of small droplets in the water phase ("coherent phase"). The viscosity of emulsions which consist only of water, oil and emulsifier, and whose content of disperse phase is below 60%, by weight, is equal to the viscosity of the coherent phase, and, in the case of oil-in-water emulsions, is thus equal to that of water. For reasons of feel on the skin, cosmetic emulsions on average comprise not more than 30% of oil phase, i.e., cosmetic emulsions are typically water-thin. Since, however, the consumer generally desires a lotion-like (high-viscosity) to cream-like (semisolid) consistency, and also the stability of emulsions increases with the viscosity of the coherent phase, the "thickening" of oil-in-water emulsions is essential. For this purpose there are two fundamentally different methods which can be combined with one another. The first method is based on the fact that certain oil-in-water emulsifiers are able, together with so-called "hydrophilic waxes", to form liquid-crystalline (lamellar) structures in the coherent water phase. Moreover, this first method forms a three dimensional network which leads to a large increase in the viscosity of the emulsion; keeps the oil droplets separate from one another; and thus improves the stability of the emulsion. Examples of "hydrophilic waxes" are stearyl alcohol, stearic acid and glyceryl stearate.

The other method is based on the ability of so-called "hydrocolloids" to take up and bind many times their own weight of water and thus lead to thickening of water. Examples of such water-swellable organopolymers are crosslinked polyacrylates ("carbomers") and polysaccharides, for example, xanthan gum. A disadvantage of these two thickening methods mentioned above is that the substances used therein can adversely affect the feel on the skin during or after application of the emulsions. Thus, for example, in the presence of relatively large amounts of hydrophilic waxes, the emulsions can only be spread with difficulty, and a dull, waxy feel on the skin often remains. On the other hand, the water-swellable organopolymers also display disadvantages in application properties. Thus, for example, in the case of carbomers, the so-called "quick-breaking effect" is observed. The "quick-breaking effect" is understood as the phenomenon where, in the case of contact of the emulsion with the electrolytes of the skin, the emulsion immediately breaks. This phenomenon is evident from an "aqueous sliding away" upon rubbing in and is often perceived as unpleasant.

For the preparation of oil-in-water emulsions, use is usually made of emulsifiers whose HLB value is between 8 and 18. The HLB value is a dimensionless parameter for characterizing surfactants and describes the ratio of the hydrophilic portion to the lipophilic portion in the molecule (HLB=hydrophilic-lipophilic balance). Thus, on the basis of numerous experiments by Griffin (J. Soc. Cosmet. Chem. 1949, 1, 311), it has been found that surfactants with an HLB value of 3 to 6 are suitable as water-in-oil emulsifiers, those with an HLB value of 6 to 8 are suitable as wetting agents, and surfactants with an HLB value of greater than 8 are suitable as oil-in-water emulsifiers. In the simplest case, the HLB value is calculated from the percentage proportion of the hydrophilic part of an emulsifier, for example, the polyethylene glycol part, by dividing this by 5. Thus, for example, the hydrophilic portion in the addition product of 20 mol of ethylene oxide (MW=880 g/mol) to stearic acid (284 g/mol) is 76%, corresponding to an HLB value of 15 (=76/5). This HLB concept has originally been limited to nonionogenic substances which contain no atoms other than carbon, hydrogen and oxygen. In addition, this FLB value definition does not apply exactly for substances whose hydrophilic part also contains propylene glycol units in addition to ethylene glycol units.

A disadvantage of emulsifiers with an HLB value of significantly greater than 8 is that such emulsifiers are less mild than emulsifiers with a lower HLB value. In addition, because of their higher hydrophilicity, emulsifiers having a HLB value of greater than 8 are more readily redispersible, i.e., they can be more readily washed off from the skin again with water, which, for example, in the case of sunscreen formulations that are supposed to be water-resistant, is undesired. Conversely, emulsifiers with an HLB value of around 8 and below form a hydrophobic film on the skin which protects the skin from excessive water loss and thus has a care effect. This is probably the main reason for the fact that water-in-oil emulsions, which require emulsifiers with an HLB value of less than 8, have a stronger care effect than oil-in-water emulsions that contain hydrophilic emulsifiers. However, oil-in-water emulsions are usually preferred by the consumer since oil-in-water emulsions can be spread more readily because of the aqueous external phase.

Oil-in-water emulsions which comprise polyether siloxanes are known from the prior art, as is shown below.

EP 0 154 837 A2 describes low-viscosity oil-in-water emulsions with a combination of a comb-like, terminally capped polyether siloxane, a surfactant with an HLB value of not less than 10, and a fatty alcohol as emulsifiers which have a low oil phase content and whose oil phase consists predominantly of silicone oil and, in addition, the water phase contains ethanol.

EP 0 279 319 A describes pigment-containing oil-in-water emulsions with a polyether siloxane as emulsifier, the polyether radical of which contains a maximum of 50 mol % of polyoxypropylene units, and whose oil phase consists predominantly of unmodified or alkyl-modified silicone oils.

EP 0 516 547 A describes oil-in-water emulsions with a comb-like polyether siloxane with an HLB value of from 9 to 12 as emulsifier, the polyether of which consists exclusively of polyethylene oxide with a terminal OH group. The oil phase consists of a chain-shaped or a cyclic siloxane.

DE 4 41 799 C1 describes cosmetic compositions that are in the form of two separate phases which are optically separate from one another, but can be combined by shaking directly prior to application to give a homogeneous emulsion and, following application, rapidly separate again into separate phases. The emulsifier used is a comb-like polyether siloxane.

EP 0 627 259 A2 discloses that silicone polyethers with an HLB value between 4 and 7 can also be used to prepare silicone-in-water emulsions. These emulsions are prepared by stirring an oil phase which consists of silicone oil and a first silicone polyether into a water phase which contains a second silicone polyether. Both silicone polyethers are comb-like in structure.

The prior art can be summarized as follows: oil-in-water emulsions with silicone polyethers as emulsifiers are known, in which the oil phase consists for the most part of silicone oils and the silicone polyether is of comb-like structure.

SUMMARY OF THE INVENTION

In a first embodiment the present invention provides a cosmetic or pharmaceutical oil-in-water emulsion which comprises one or more polyether siloxanes of the general formula (I)

$$R(CH_3)_2SiO—[(CH_3)_2SiO]_n—Si(CH_3)_2R \quad (I)$$

where n=50 to 250

$R=—(CH_2)_m—O—(C_2H_4O)_x—(C_3H_6O)_yR^1$ m=2 to 4 x=3 to 100 y=0 to 50

$R^1$=H, $CH_3$, or $CH_2CH_3$, having a proportion, by weight, of the polyether radicals R of up to 45%, by weight, of the total molecular mass, calculated according to formula (II):

"proportion by weight" (in %) of the polyether radicals R of the total molecular mass= $(MW_{polyether\ radicals}/MW_{total})\cdot 100$ (II)

where $MW_{total}=MW_{silicone\ radical}+MW_{polyether\ radicals}$ $MW_{silicone\ radical}=n\cdot 74.1+132.2$ $MW_{polyether\ radicals}=2\cdot(m\cdot 14+16+x\cdot 44+y\cdot 58+z)$ where z=1, 15 or 29.

A further embodiment of the present invention is directed to cosmetic or pharmaceutical oil-in-water emulsions comprising (a) one or more polyether siloxanes of the general formula (I);
(b) liquid-crystalline-structure-forming hydrophilic waxes, and/or water-swellable organopolymers as bodying agents and stabilizers;
(c) cosmetic oils and waxes; and
(d) customary auxiliaries and active ingredients.

DETAILED DESCRIPTION OF THE INVENTION

Figure 1:
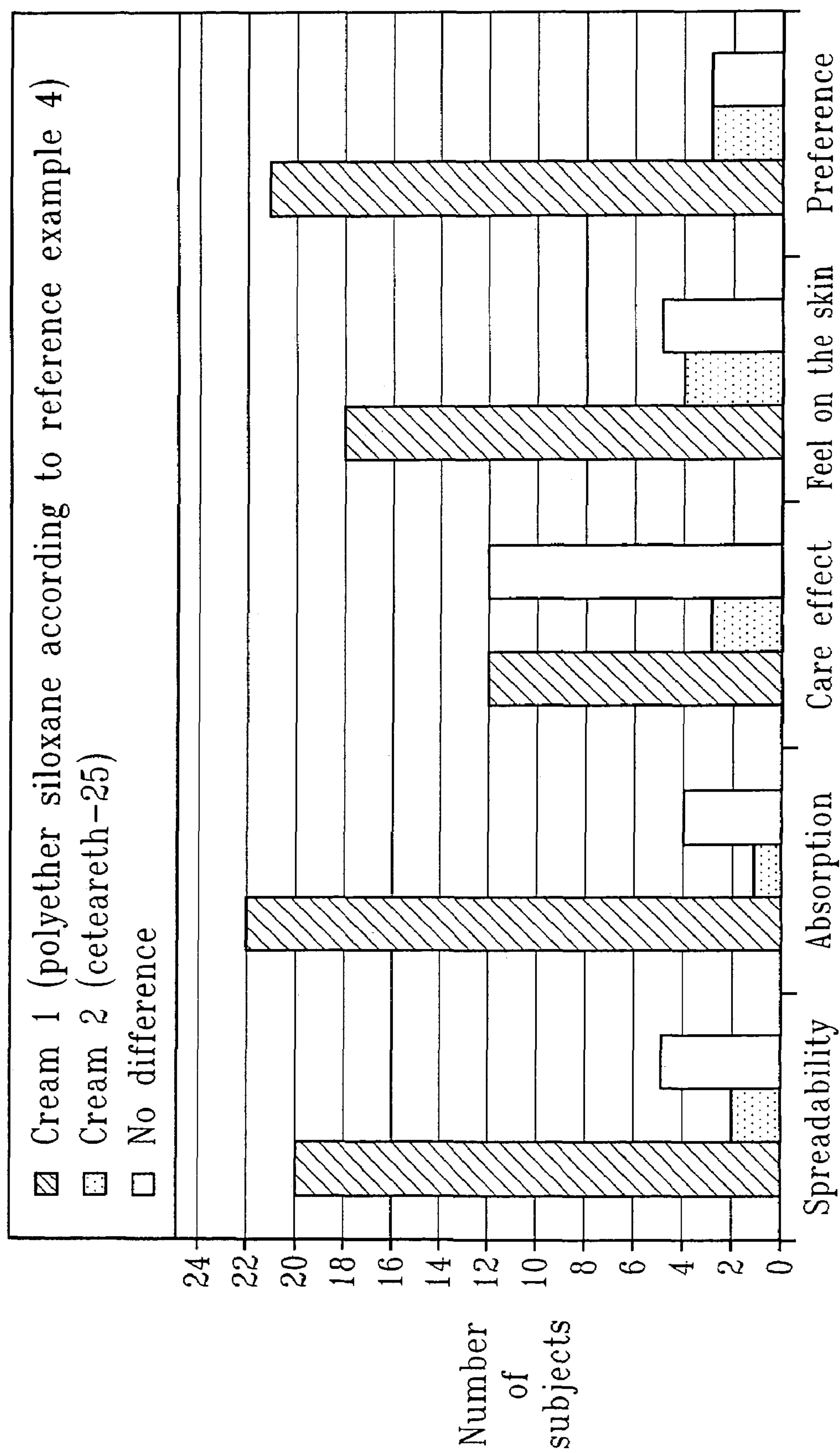
FIG. 1 shows the results of the panel test with creams 1 & 2 prepared in Example 12.

Surprisingly, applicants have determined that by using hydrophobic polyether-modified polysiloxanes of a defined structure as an emulsifier-active component, it is possible to obtain homogeneous and stable oil-in-water emulsions, in particular oil-in-water emulsions, which contain substantially little or no silicone compounds as oil components. In addition, it is surprising that by using this special type of polyether siloxanes (see, formula I above), the consistency-imparting structures customary in cosmetic oil-in-water emulsions, be they the liquid-crystalline structures of the hydrophilic waxes or the gel structures formed from water-swellable organopolymers, are less disturbed than using customary hydrophilic polyether siloxanes. This disruption is evident, for example, from a gritty appearance directly following preparation of an emulsion whose cream-like consistency has been produced using hydrophilic waxes or, in the case of water-swellable organopolymers, from a lower viscosity of the emulsion. In addition, it could not have been foreseen that the polyether siloxanes used according to the present invention minimize or even eliminate completely the disadvantages in application properties caused by customary bodying agents, such as, for example, the rough-waxy feel on the skin, the "quick-breaking effect" and the "whitening" (=foaming upon rubbing in). Moreover, it is quite surprising and totally unexpected that the modified polyether siloxanes of formula (I) are capable of positively influencing the feel on the skin. The skin feels, particularly after rubbing in of the inventive emulsion ("afterfeel"), velvety-silky and extremely smooth, which, in addition, is also retained for a long period. This unique feel on the skin is not achieved using standard commercial organic emulsifiers or others than the $\alpha,\omega$-polyether siloxanes used according to the present invention, even in combination with oil-soluble silicone compounds such as, for example, cyclic or chain-shaped polydimethylsiloxanes. A particular embodiment of the present invention therefore covers oil-in-water emulsions which are free from silicone-like oil components.

Because of the preferably hydrophobic character of these polyether siloxanes, it is also to be expected that the inventive polyether siloxanes are particularly mild on the skin, and form a hydrophobic film on the skin which protects the skin from drying out. Since the resultant film is difficult to remove with water, the films which are derived from the inventive polyether siloxanes are particularly useful as water-resistant sunscreen preparations.

From earlier work in the prior art, it is known that polyether siloxanes, irrespective of type, are, alone without coemulsifiers, unable, to interplay with hydrophilic waxes such as stearyl alcohol or glycerol stearate, to form liquid-crystalline structures in the coherent water phase and thus do not produce the required lotion- or cream-like consistency and also stability. It was, however, surprising that this is possible using just a small proportion of a coemulsifier, and that homogeneous and long-term-stable emulsions can be obtained using only the polyether siloxanes according to the present invention. In a comparison experiment with, for example, a comb-like hydrophilic siloxane, the cream, following preparation and cooling, was considerably inhomogeneous and gritty.

To distinguish exactly the polyether siloxanes used according to the present invention from the polyether siloxanes known from the prior art and used for the preparation of oil-in-water emulsions, the inventors have dispensed with stating an HLB value in favor of stating the proportion by weight of the polyether radicals based on the total molecular weight, because a classical calculation of the HLB value would be incorrect since this class of emulsifiers contains silicon atoms and, in addition, propylene glycol units are also permitted in the polyether radical. A characterization using the so-called "three-dimensional HLB concept" by A. J. O'Lenick et al. (Cosm. & Toil., 111, 1996, 37–44) does not appear very useful either. This is because this system predicts that no stable oil-in-water or water-in-oil emulsions can be obtained using silicone polyethers since silicone polyethers do not contain components which are soluble in a purely organic oil phase. This is specifically contradicted by the use according to the present invention of the polyether siloxanes described below. In the "three-dimensional HLB concept", a silicone-soluble component is also taken into consideration, in addition to the water- and oil-soluble component of an emulsifier. An emulsifier is thus already characterized unambiguously by an HLB value for the water-soluble portion (0–20) and an HLB value for the oil-soluble portion (0–20), the HLB value for the silicone-soluble portion arising from the difference between 20 and the sum of the HLB values for the water- and oil-soluble portion. In a right-angled triangle whose hypotenuse represents the classical HLB scale from 0 to 20, the areas with the corresponding HLB values of the emulsifier, in which stable emulsions of a certain type are obtained, are enclosed. Possible types of emulsions are water-in-oil, oil-in-water, water-in-silicone, silicone-in-water, oil-in-silicone and silicone-in-oil. From the HLB triangle, it is. for example, clear that silicone polyethers (the HLB value for the oil-soluble portion is in this case 0) with an HLB value of from 9 to 18 for the water-soluble portion produce silicone-in-water emulsions, but with an HLB value of from 3 to 6, water-in-silicone emulsions are produced. In addition, it can be deduced therefrom that by using silicone polyethers, no stable oil-in-water or water-in-oil emulsions should be obtained. This seems obvious since silicone polyethers contain no components which are soluble in an organic oil phase. This also explains why the prior art has hitherto described only emulsions with silicone polyethers which exclusively or predominantly contain silicone oil as the second phase in addition to the water phase. The polyether siloxanes used according to the present invention are notable for the fact that, in contrast to the silicone polyethers used in the prior art, the inventive polyether siloxanes are not comb-like, but carry the polyether radicals at the two ends based on the linear unbranched silicone chain, and the proportion by weight of the polyether radicals of the total molecular mass is less than or equal to 45%. The emulsions according to the present invention can also comprise one or more coemulsifiers, but in a lower proportion than the polyether siloxanes used according to the present invention, and also bodying agents and stabilizers typical for cosmetic emulsions.

In a further embodiment, the present invention is directed to emulsions which comprise polyether siloxanes of the general formula (I) in combination with additional emulsifiers, where the proportion of the polyether siloxanes of the general formula (I) based on the sum of total emulsifiers is more than 50%, by weight, preferably 65 to 90%, by weight.

Additional emulsifiers that can be employed in the present invention are, for example, nonionogenic surfactants selected from at least one of the following groups:

comb-like polyether siloxanes;

addition products from 2 to 30 mol of ethylene oxide and/or 0 to 5 mol of propylene oxide to linear fatty alcohols having 8 to 22 carbon atoms, to fatty acids having 12 to 22 carbon atoms and to alkylphenols having 8 to 15 carbon atoms in the alkyl group;

C12/18-fatty acid mono- and diesters of addition products of from 1 to 30 mol of ethylene oxide to glycerol;

glycerol mono- and diesters and sorbitan mono- and diesters of saturated and unsaturated fatty acids having 6 to 22 carbon atoms and the ethylene oxide addition products thereof;

alkyl mono- and oligoglycosides having 8 to 22 carbon atoms in the alkyl radical and the ethoxylated analogs thereof;

addition products of from 15 to 60 mol of ethylene oxide with castor oil and/or hydrogenated castor oil;

polyol and, in particular, polyglycerol esters, such as, for example, polyglycerol polyricinoleate, polyglycerol 12-hydroxystearate or polyglycerol dimerate. Also suitable are mixtures of compounds from two or more of these classes of substances;

addition products of from 2 to 15 mol of ethylene oxide to castor oil and/or hydrogenated castor oil;

partial esters based on linear, branched, unsaturated or saturated C6/22-fatty acids, ricinoleic acid and 12-hydroxystearic acid and glycerol, polyglycerol, pentaerythritol, dipentaerythritol, sugar alcohols (for example sorbitol), alkylglucosides (for example methylglucoside, butylglucoside, laurylglucoside), and polyglucosides (for example cellulose);

mono-, di- and trialkyl phosphates, and mono-, di- and/or tri-PEG alkyl phosphates and salts thereof;

wool wax alcohols;

polysiloxane-polyalkyl-polyether copolymers, or corresponding derivatives;

mixed esters of pentaerythritol, fatty acids, citric acid and fatty alcohol according to German patent 11 65 574 and/or mixed esters of fatty acids having 6 to 22 carbon atoms, methylglucose and polyols, preferably glycerol or polyglycerol:

polyalkylene glycols;

betaines;

esterquats; and sodium, potassium or ammonium salts of long-chain alkylsulfonic and alkyl ether sulfonic acids.

The addition products of ethylene oxide and/or of propylene oxide to fatty alcohols, fatty acids, alkyl phenols, glycerol mono- and diesters and sorbitanmono- and diesters of fatty acids or to castor oil are known, commercially available products. These addition products are homolog mixtures, the average degree of alkoxylation of which corresponds to the ratio of the amounts of ethylene oxide and/or propylene oxide and substrate with which the addition reaction is carried out.

Furthermore, zwitterionic surfactants can be used as emulsifiers. Zwitterionic surfactants is the term used to refer to surface-active compounds which carry at least one quaternary ammonium group and at least one carboxylate and one sulfonate group in the molecule. Particularly suitable zwitterionic surfactants are the so-called betaines, such as: the N-alkyl-N,N-dimethylammonium glycinates, for example, cocoalkyldimethylammonium glycinate; N-acylaminopropyl-N,N-dimethylammonium glycinates, for example, cocoacylaminopropyldimethyl-ammonium glycinate; and 2-alkyl-3-carboxylmethyl-3-hydroxyethylimidazolines having in each case 8 to 18 carbon atoms in the alkyl or acyl group; and cocoacylaminoethyl hydroxyethylcarboxymethylglycinate. Particular preference is given to the fatty acid amide derivative known under the CTFA name Cocamidopropyl Betaine.

Likewise suitable emulsifiers are ampholytic surfactants. Ampholytic surfactants is understood as meaning those surface-active compounds which, apart from a C8/18-alkyl or -acyl group in the molecule, contain at least one free amino group and at least one COOH or $SO_3H$ group and are capable of forming internal salts. Examples of suitable ampholytic surfactants are N-alkylglycine; N-alkylpropionic acids; N-alkylaminobutyric acids; N-alkyliminodipropionic acids; N-hydroxyethyl-N-alkylamidopropylglycines; N-alkyltaurines; N-alkylsarcosines; 2-alkylaminopropionic acids; and alkylaminoacetic acids having in each case about 8 to 18 carbon atoms in the alkyl group. Particularly preferred ampholytic surfactants are N-cocoalkylaminopropionate, cocoacylaminoethylaminopropionate and C12/18-acylsarcosine. In addition to the ampholytic emulsifiers, quaternary emulsifiers are also suitable, with those of the esterquat type being particularly preferred. More preferably methyl-quaternized difatty acid triethanolamine ester salts are employed.

A further embodiment of the oil-in-water emulsions according to the present invention include hydrophilic waxes chosen from the group consisting of stearyl alcohol, stearic acid and/or glyceryl stearate as bodying agents, and, as coemulsifiers, an organic emulsifier which is able to form liquid-crystalline structures together with the hydrophilic waxes. Preference is given to a proportion of from 5 to 49% by weight of the organic coemulsifier of the total amount of the emulsifiers, particular preference to a proportion of from 10 to 35% by weight. The proportion of the polyether siloxane used according to the present invention is at least 51% by weight of the total amount of the emulsifiers.

Suitable bodying agents are primarily fatty alcohols or hydroxyl fatty alcohols having 12 to 22, and preferably 16 to 18, carbon atoms, and also partial glycerides, fatty acids or hydroxy fatty acids. Suitable thickeners are, for example, polysaccharides, in particular, xanthan gum, guar guar, agar agar, alginates and tyloses; carboxymethylcellulose and hydroxyethylcellulose. Also, higher molecular weight polyethylene glycol mono- and diesters of fatty acids, polyacrylates (for example carbopols from Goodrich, TEGO carbomers from Goldschmidt or Synthalens from Sigma); polyacrylamides; polyvinyl alcohol; and polyvinylpyrrolidone, surfactants such as, for example, ethoxylated fatty acid glycerides, esters of fatty acids with polyols such as, for example, pentaerythritol or trimethylolpropane, fatty alcohol ethoxylates having a narrowed homolog distribution, or alkyl oligoglucosides may be employed herein.

Suitable as the oil phase are, for example, those oil components which are known as cosmetic and pharmaceutical oil components and as components of lubricants. These include, in particular, mono- or diesters of linear and/or branched mono- and/or dicarboxylic acids having 2 to 44 carbon atoms with linear and/or branched saturated or unsaturated alcohols having 1 to 22 carbon atoms. Also suitable within the meaning of the present invention are the esterification products of aliphatic difunctional alcohols having 2 to 36 carbon atoms with monofunctional aliphatic carboxylic acids having 1 to 22 carbon atoms. Monoesters suitable as oil components are, for example, the methyl esters and isopropyl esters of fatty acids having 12 to 22 carbon atoms, such as, for example, methyl laurate, methyl stearate, methyl oleate, methyl erucate, isopropyl palmitate, isopropyl myristate, isopropyl stearate, and isopropyl oleate. Other suitable monoesters include, but are not limited to: n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, and esters obtainable from industrial aliphatic alcohol cuts and industrial, aliphatic carboxylic acid mixtures, for example, esters of unsaturated fatty alcohols having 12 to 22 carbon atoms and saturated and unsaturated fatty acids having 12 to 22 carbon atoms, as are accessible from animal and vegetable fats. Also suitable are naturally occurring monoester or wax ester mixtures, as are present, for example, in jojoba oil or in sperm oil.

Suitable dicarboxylic esters include, but are not limited to: di-n-butyl adipate, di-n-butyl sebacate, di-(2-ethylhexyl) adipate, di-(2-hexyldecyl) succinate, D-isotridecyl acelate. Suitable diol esters are, for example, ethylene glycol dioleate, ethylene glycol diisotridecanoate, propylene glycol di-(2-ethyl hexanoate), butanediol diisostearate and neopentyl glycol dicaprylate.

Also suitable as oil component are the fatty acid triglycerides, where, among these, the naturally occurring oils and fats are preferred. Suitable oil components include natural, vegetable oils, for example olive oil, sunflower oil, soy oil, peanut oil, rapeseed oil, almond oil, palm oil or else the liquid fraction of coconut oil or of palm kernel oil; and animal oils, such as, for example, neat's foot oil, the liquid fractions of beef tallow or also synthetic triglycerides of caprylic/capric acid mixtures, triglycerides of technical-grade oleic acid or of palmitic acid/oleic acid mixtures.

Suitable further auxiliaries and additives are, inter alia, UV light protection filters which are well known to those skilled in the sunscreen art.

UV light protection filters are understood as meaning organic substances which are able to absorb ultraviolet rays and re-emit the absorbed energy in the form of long-wave radiation, for example heat. UVB filters may be oil-soluble or water-soluble. Examples of oil-soluble substances are:

- 3-benzylidenecamphor and derivatives thereof, for example 3-(4-methylbenzylidene)camphor;
- 4-aminobenzoic acid derivatives, preferably 2-ethylhexyl 4-(dimethylamino)benzoate, 2-ethylhexyl 4-(dimethylamino)benzoate and amyl 4-(dimethylamino)benzoate;
- esters of cinammic acid, preferably 2-ethylhexyl 4-methoxycinnamate, isopentyl 4-methoxycinnamate, 2-ethylhexyl 2-cyano-3-phenylcinnamate (octocrylene);
- esters of salicylic acid, preferably 2-ethylhexyl salicylate, 4-isopropylbenzyl salicylate, homomenthyl salicylate;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably di-2-ethylhexyl 4-methoxybenzalmalonate;
- triazine derivatives, such as[, for example,] 2,4,6-trianilino-(p-carbo-2'-ethyl-1'-hexyloxy)-1,3,5-triazine and octyltriazone; and
- propane-1,3-diones, such as 1-(4-tertbutylphenyl)-3-(4'-methoxyphenyl)propane-1,3-dione.

Suitable water-soluble substances are:

- 2-phenylbenzimidazole-5-sulfonic acid and the alkali metal, alkaline earth metal, ammonium, alkylammonium, alkanolammonium and glucammonium salts thereof;
- sulfonic acid derivatives of benzophenone, preferably 2-hydroxy-4-methoxybenzophenone-5-sulfonic acid and its salts; and
- sulfonic acid derivatives of 3-benzylidenecamphor, such as, for example, 4-(2-oxo-3-bornylidenemethyl)benzenesulfonic acid and 2-methyl-5-(2-oxo-3-bornylidene) sulfonic acid and salts thereof.

Suitable typical UV-A filters are, in particular, derivatives of benzoyl methane, such as 1-(4'-tert-butylphenyl)-3-(4'-methoxyphenyl)propane-1,3-dione or 1-phenyl-3-(4'-isopropylphenyl)propane-1,3-dione. The UV-A and UV-B filters can of course also be used in mixtures. In addition to said soluble substances, insoluble pigments, namely finely dispersed metal oxides or salts, are also suitable for this purpose, such as, for example, titanium dioxide, zinc oxide, iron oxide, aluminum oxide, cerium oxide, zirconium oxide, silicates (talc), barium sulfate and zinc stearate. Here, the particles of the UV filters should have an average diameter of less than 100 nm, preferably between 5 and 50 nm and in particular between 15 and 30 nm. The UV filters may have a spherical shape, although it is also possible to use particles which have an ellipsoidal shape or a shape which deviates in some other way from the spherical form. A relatively new class of light protection filters are micronized organic pigments, such as, for example, 2,2'-methylenebis-{6-(2H-benzotriazol-2-yl)-4-(1,1,3,3-tetramethylbutyl)phenol} having a particle size of less than 200 nm, which is available, for example, as a 50% strength aqueous dispersion.

In addition to the two abovementioned groups of primary light protection filters, it is also possible to use secondary light protection agents of the antioxidant type, which interrupt the photochemical reaction chain which is triggered when UV radiation penetrates into the skin. Typical examples thereof are amino acids (for example, glycine, histidine, tyrosine, tryptophan) and derivatives thereof, imidazole (for example, urocanic acid) and derivatives thereof, peptides such as D,L-carnosine, D-carnosine and derivatives thereof (for example anserine), carotinoids, carotenes (for example, α-carotene, β-carotene, lycopene) and derivatives thereof, chlorogenic acid and derivatives thereof, lipoic acid and derivatives thereof (for example, dihydrolipoic acid), aurothioglucose, propylthiouracil and other thiols (for example, thioredoxin, glutathione, cysteine, cystine, cystamine and the glycosyl, n-acetyl, methyl, ethyl, propyl, amyl, butyl and lauryl, palmitoyl, oleyl, γ-linoleyl, cholesteryl and glyceryl esters thereof) and salts thereof, dilauryl thiopropionate, distearyl thiopropionate, thiodipropionic acid and derivatives thereof (esters, ethers, peptides, lipids, nucleotides, nucleosides and salts) and sulfoximine compounds (for example, buthionine sulfoximines, homocysteine sulfoximine, buthionine sulfones, penta, hexa, heptathionine sulfoximine) in very low tolerated doses (for example, pmol to μmol/kg), and also (metal) chelating agents (for example, α-hydroxy fatty acids, palmitic acid, phytic acid, lactoferric acid), α-hydroxy acids (for example citric acid, lactic acid, malic acid), humic acid, bile acid, bile extracts, bilirubin, biliverdin, EDTA, EGTA and derivatives thereof, ubiquinone and ubiquinol and derivatives thereof, vitamin C and derivatives (e.g., ascorbyl palmitate, Mg ascorbyl phosphate, ascorbyl acetate), tocopherols and derivatives (for example, vitamin E acetate), vitamin A and derivatives (vitamin A palmitate), and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (for example, Zno, $ZnSO_4$), selenium and derivatives thereof (for example, selenomethionine), stilbenes and derivatives thereof (for example, stilbene oxide, trans-stilbene oxide) and the derivatives (salts, esters, ethers, sugars, nucleotides, peptides and lipids) of said active ingredients which are suitable according to the invention.

Suitable preservatives that may be employed in the present invention are, for example, phenoxyethanol, formaldehyde solution, parabens, pentanediol or sorbic acid.

Suitable insect repellents that may be employed herein are N,N-diethyl-m-toluamide, 1,2-pentanediol or Insect Repellent 3535, suitable self-tanning agents are dihydroxyacetone, and perfume oils which may be mentioned are mixtures of natural and synthetic fragrances. Natural fragrances are extracts from flowers (lily, lavender, rose, jasmine, neroli, ylang ylang), stems and leaves (geranium, patchouli, petitgrain), fruits (aniseed, coriander, caraway, juniper), fruit peels (bergamot, lemons, oranges), roots (mace, angelica, celery, cardamom, costus, iris, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are e.g., benzyl acetate, phenoxyethyl isobutyrate, p-tert-butylcyclohexyl acetate, linalyl acetate, dimethyl-benzyl-carbinyl acetate, phenylethyl acetate, linalyl benzoate, benzyl formate, ethyl methylphenylglycidate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include predominately the terpenes and balsams. However, preference is given to using mixtures of different fragrances which together produce a pleasing scent note. Essential oils of relatively low volatility, which are mostly used as aroma components, are also suitable as perfume oils, for example, sage oil, camomile oil, oil of cloves, balm oil, mint oil, cinnamon leaf oil, lime blossom oil, juniperberry oil, vertiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamenaldehyde, linalool, boisambrene forte, ambroxan, indole, Hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, Iso-E-Super, Fixolide NP, Evernyl, iraldein gamma, phenylacetic acid, geranyl acetate, benzyl acetate, rose oxide, Romillat, Irotyl and Floramat alone or in mixtures.

Suitable deodorant active ingredients that are contemplated herein are e.g., odor-masking agents, such as the customary perfume constituents, odor absorbers, for example, the phyllosilicates described in laid-open patent specification DE-P 40 09 347, and of these, in particular, montmorillonite, kaolinite, illite, beidellite, nontronite, saponite, hectorite, bentonite, smectite, and also, for example, zinc salts of ricinoleic acid. Antibacterial agents are also suitable for incorporation into the oil-in-water emulsions according to the present invention. Advantageous substances are, for example, 2,4,4'-trichloro-2'-hydroxydiphenyl ether (Irgasan), 1,6-di(4-chlorophenylbiguanido) hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol) and the active agents described in patent laid-open specifications DE-198 55 934, DE-37 40 186, DE-39 38 140, DE-42 04 321, DE-42 29 707, DE-42 29 737, DE-42 38 081, DE-43 09 372 and DE-43 24 219. Further customary antiperspirant active ingredients can likewise be advantageously used in the preparations according to the present invention, in particular astringents, for example, basic aluminum chlorides, such as aluminum chlorohydrate ("ACH") and aluminum zirconium glycine salts ("ZAG").

Dyes which may be used are the substances permitted and suitable for cosmetic purposes, as listed, for example, in the publication "Kosmetische Färbemittel" from the Farbstoffkommission der Deutschen Forschungsgemeinschaft, Verlag Chemie, Weinheim, 1984, pp. 81–106. These dyes are customarily used in concentrations of from 0.001 to 0.1% by weight, based on the total mixture.

Examples of suitable active ingredients are tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

A further embodiment of the oil-in-water emulsions according to the invention covers those which are free from oil-soluble silicone compounds, in particular volatile cyclic polydimethylsiloxanes.

The following examples are given to illustrate the present invention as well as to show certain advantages that may be obtained therefrom.

EXAMPLES

Reference Examples 1 to 5

Examples of polyether siloxanes of the general formula (I) used according to the present invention are listed in the table below:

| Example | n | $MW_{silicone\ radical}$ | m | x | y | z | $MW_{polyether\ radicals}$ | Proportion by weight of polyether radicals in [%]* |
|---|---|---|---|---|---|---|---|---|
| 1 | 66 | 5048 | 3 | 13 | 0 | 1 | 1262 | 20 |
| 2 | 50 | 3837 | 3 | 15 | 10 | 15 | 2626 | 41 |
| 3 | 200 | 14952 | 3 | 13 | 20 | 1 | 3582 | 19 |
| 4 | 100 | 7542 | 3 | 11 | 17 | 1 | 3058 | 29 |
| 5 | 150 | 11247 | 3 | 19 | 3 | 29 | 2194 | 16 |

*calculated according to formula (II)

Examples of oil-in-water emulsions according to the present invention are listed below:

Example 1

| | | |
|---|---|---|
| A | Polyether siloxane reference example 5 | 2.0% |
| | Caprylic/capric triglyceride | 10.4% |
| | Ethylhexyl stearate | 5.0% |
| | Mineral oil (30 mPas) | 5.0% |
| | Tocopheryl acetate | 1.0% |
| B | Glycerol | 2.0% |
| | Panthenol | 1.0% |
| | Allantoin | 0.1% |
| | Alcohol (ethanol) | 10.0% |
| | Water | 66.2% |
| C | TEGO ® Carbomer 140 (carbomer) | 0.15% |
| | TEGO ® Carbomer 141 (carbomer) | 0.15% |
| | Xanthan gum | 0.1% |
| | Ethylhexyl stearate | 1.6% |
| D | Sodium hydroxide (10% in water) | 0.7% |
| | Preservative, perfume | q.s. |

Example 2

| | | |
|---|---|---|
| A | Polyether siloxane reference example 4 | 2.3% |
| | ABIL ® B 8863[1)] | 0.3% |
| | Caprylic/capric triglyceride | 10.4% |
| | Isohexadecane | 5.0% |
| B | Water | 79.3% |
| C | TEGO ® Carbomer 140 (carbomer) | 0.3% |
| | Xanthan gum | 0.1% |
| | Mineral oil (30 mPas) | 1.6% |
| D | Sodium hydroxide (10% in water) | 0.7% |
| | Preservative, perfume | q.s. |

[1)]ABIL ® B 8863: comb-like polyether siloxane with a proportion by weight of the polyether radicals of the total molecular mass of 76%.

Example 3

| | | |
|---|---|---|
| A | Polyether siloxane reference example 1 | 2.0% |
| | C12–15-Alkyl benzoate | 3.0% |
| | Decyl cocoate | 2.0% |
| | Isopropyl palmitate | 0.4% |
| | Avocado oil | 1.0% |
| | 4-Methylbenzylidenecamphor | 3.0% |
| | Ethylhexyl methoxycinnamate | 2.5% |
| | Isoamyl p-methoxycinnamate | 2.5% |
| | Butylmethoxydibenzoylmethane | 2.0% |
| | Tocopheryl acetate | 0.5% |
| B | TEGO ® SMO 80 (Polysorbate 80) | 0.2% |
| | Glycerol | 2.0% |
| | EDTA | 0.1% |
| | GluCare ® S (sodium carboxymethyl betaglucan) | 0.1% |
| | Water | 75.9% |
| C | TEGO ® Carbomer 140 (carbomer) | 0.15% |
| | TEGO ® Carbomer 141 (carbomer) | 0.15% |
| | Xanthan gum | 0.1% |
| | Isopropyl palmitate | 1.6% |
| D | Sodium hydroxide (10% in water) | 0.8% |
| | Preservative, perfume | q.s. |

Example 4

| | | |
|---|---|---|
| A | Polyether siloxane reference example 2 | 2.0% |
| | C12–15 Alkyl benzoate | 3.0% |
| | Decyl cocoate | 2.0% |
| | Isopropyl palmitate | 0.4% |
| | Avocado oil | 1.0% |
| | Ethylhexyl methoxycinnamate | 5.0% |
| | Isoamyl p-methoxycinnamate | 5.0% |
| | Tocopheryl acetate | 0.5% |
| B | TEGO ® SMO 80 (Polysorbate 80) | 0.2% |
| | Glycerol | 2.0% |
| | GluCare ® S (betaglucan) | 0.1% |
| | Water | 68.6% |
| C | TEGO ® Carbomer 140 (carbomer) | 0.15% |
| | TEGO ® Carbomer 141 (carbomer) | 0.15% |
| | Xanthan gum | 0.1% |
| | Isopropyl palmitate | 1.6% |

-continued

| | | |
|---|---|---|
| D | Tinosorb ® M (methylenebisbenzotri-azolyhetramethylbutylphenol) (50%) | 8.0% |
| E | Sodium hydroxide (10% in water) | 0.8% |
| | Preservative, perfume | q.s. |

Example 5

| | | |
|---|---|---|
| A | Polyether siloxane reference example 3 | 1.5% |
| | TEGINACID ® C (ceteareth-25) | 0.5% |
| | Stearyl alcohol | 2.0% |
| | Glyceryl stearate | 1.0% |
| | Stearic acid | 1.0% |
| | Isopropyl palmitate | 5.0% |
| | Ethylhexyl stearate | 5.0% |
| | Mineral oil (30 mPas) | 3.2% |
| | Tocopheryl acetate | 0.3% |
| B | Glycerol | 2.0% |
| | Panthenol | 0.5% |
| | Allantoin | 0.2% |
| | Water | 76.96% |
| C | TEGO ® Carbomer 134 (carbomer) | 0.1% |
| | Mineral oil (30 mPas) | 0.4% |
| D | Sodium hydroxide (10% water) | 0.25% |
| | Preservative, perfume | q.s. |

Example 6

| | | |
|---|---|---|
| A | Polyether siloxane reference example 1 | 1.5% |
| | PEG-100 stearate | 0.5% |
| | Stearyl alcohol | 2.0% |
| | Stearic acid | 2.0% |
| | Caprylic/capric triglyceride | 7.0% |
| | Ethylhexyl stearate | 6.2% |
| | Tocopheryl acetate | 0.3% |
| B | Glycerol | 2.0% |
| | Panthenol | 0.5% |
| | Allantoin | 0.2% |
| | Water | 76.96% |
| C | TEGO ® Carbomer 134 (carbomer) | 0.1% |
| | Mineral oil (30 mPas) | 0.4% |
| D | Sodium hydroxide (10% in water) | 0.25% |
| | Preservative, perfume | q.s. |

Example 7

| | | |
|---|---|---|
| A | Polyether siloxane reference example 4 | 1.5% |
| | TEGINACID ® C (ceteareth-25) | 0.5% |
| | Stearyl alcohol | 1.5% |
| | Glyceryl stearate | 2.5% |
| | Stearyl heptanoate | 3.0% |
| | Cetearyl ethylhexanoate | 7.0% |
| | Decyl oleate | 3.5% |
| B | Glycerol | 3.0% |
| | Panthenol | 0.5% |
| | Water | 76.16% |
| C | TEGO ® Carbomer 134 (carbomer) | 0.1% |
| | Mineral oil (30 mPas) | 0.4% |
| D | Sodium hydroxide (10% in water) | 0.25% |
| | Preservative, perfume | q.s. |

Example 8, Comparative Examples 1 and 2

| | Examples | Comp.1 | Comp.2 | 8 |
|---|---|---|---|---|
| A | Polyether siloxane Reference example 3 | — | — | 1.8% |
| | ABIL ® B 8863[1)] | 1.8% | 1.8% | — |
| | Ceteareth-25 | — | 0.2% | 0.2% |
| | Glyceryl stearate | 2.0% | 2.0% | 2.0% |
| | Stearyl alcohol | 1.0% | 1.0% | 1.0% |
| | Mineral oil | 5.0% | 5.0% | 5.0% |
| | Ethylhexyl stearate | 5.0% | 5.0% | 5.0% |
| | Isopropyl palmitate | 5.0% | 5.0% | 5.0% |
| B | Glycerol | 2.0% | 2.0% | 2.0% |
| | Water | 80.0% | 80.0% | 80.0% |

[1)] ABIL ® B 8863: Comb-like polyether siloxane with a proportion by weight of the polyether radicals of the total molecular mass of 76%.

Preparation: Phase A and phase B were heated separately to 70° C. and combined, and the mixture was intensively homogenized for 1 min. It was then cooled in a water bath with stirring. The emulsion of comparative example 1 remained water-thin after cooling, and the bodying agents were present as inhomogeneous lumps. The emulsion of comparative example 2 was cream-like solid, although the emulsion was extremely inhomogeneous and gritty, while the emulsion of example 8 according to the present invention had a smooth and homogeneous appearance after cooling to room temperature.

This comparison shows that creams containing the polyether siloxane of reference example 3 used in accordance with the present invention in combination with the organic coemulsifier ceteareth-25 can be prepared without problems by the hot method, while creams containing a combination of the polyether siloxane ABIL® B 8863 with ceteareth-25 cannot be prepared.

Example 9, Comparative Examples 3 and 4

| | Examples | 9 | Comp.3 | Comp.4 |
|---|---|---|---|---|
| A | Polyether siloxane Reference example 3 | 1.0% | | |
| | Hostaphat ® KL 340 N (trilaureth-4 phosphate) | | 1.0% | |
| | ABIL ® B 8852[1)] | | | 1.0% |
| | Mineral oil | 8.0% | 8.0% | 8.0% |
| | Octyl palmitate | 5.0% | 5.0% | 5.0% |
| | Caprylic/Capric triglyceride | 6.0% | 6.0% | 6.0% |
| B | Glycerol | 2.8% | 2.8% | 2.8% |
| | Water | 75.0% | 75.0% | 75.0% |
| C | Sodium hydroxide (10% in water) | 0.7% | 0.7% | 0.7% |
| D | TEGO ® Carbomer 140 (carbomer) | 0.2% | 0.2% | 0.2% |
| | Xanthan gum | 0.2% | 0.2% | 0.2% |
| | Octyl palmitate | 1.1% | 1.1% | 1.1% |

[1)] ABIL ® B 8852: Comb-like polyether siloxane with a proportion by weight of the polyether radicals of the total molecular mass of 67%.

Preparation: Phase A was mixed until it was homogeneous and then added to phase B. The mixture was homogenized intensively. Phase C was then added with gentle stirring. Finally, phase D was added, and the mixture was briefly homogenized again.

Following preparation, the formulation according to example 9 gave a smooth, homogeneous emulsion with a viscosity of 9.0 Pas, and the formulation according to comparative example 3 gave a smooth, homogeneous emulsion with a viscosity of 4.5 Pas. The formulation according to comparative example 4 gave, following the addition of the carbomer/xanthan gum dispersion, a glassy and inhomogeneous emulsion which separated after just a few minutes.

This comparison shows that the thickening and stabilizing action of hydrocolloids such as carbomers or xanthan gum is influenced by emulsifiers in different ways. Their action is virtually not impaired by the silicone polyethers used according to the present invention; their thickening action is impaired by a commercially available organic emulsifier, and, by contrast, the commercially available comb-like silicone polyether ABIL® B 8852 suppresses even the stabilizing action.

Example 10

In a panel test, 20 subjects were asked to compare two body lotions with regard to the application properties. One lotion comprised 2% of the polyether siloxane according to reference example 3 as emulsifier, and the other lotion comprised a commercially available organic emulsifier Eumulgin® VL 75 (compound of lauryl glucoside, polyglycerol-2 dipolyhydroxystearate, glycerol and water, 4% corresponding to 2% of emulsifier-active components); otherwise the formulations were identical.

Result: With regard to the spreadability and the absorption behavior, the two lotions were evaluated as virtually the same; however, the feel on the skin following complete absorption of the lotions was evaluated in the case of the polyether siloxane as smoother/softer and more velvety/silkier than in the case of the organic emulsifier. 17 of the 20 subjects would choose the lotion containing the polyether siloxane in preference.

Example 11

In a panel test, 5 subjects were asked to compare two body lotions with regard to the application properties. One lotion comprised 3% of the polyether siloxane according to reference example 5 as emulsifier, and the other lotion comprised a commercially available polyether siloxane, ABIL B 8843 (comb-like polyether siloxane with a proportion by weight of the polyether radicals of the total molecular mass of 67%); otherwise the formulations were identical.

Result: With regard to the spreadability and the absorption behavior, the two lotions were evaluated as virtually the same; however, the feel on the skin following complete absorption of the lotions was evaluated in the case of the polyether siloxane according to the invention as smooth/soft and velvety/silky, while the feel on the skin in the case of the commercially available polyether siloxane was evaluated as dry and rough. All 5 subjects preferred the lotion containing the polyether siloxane according to the invention.

Example 12

In a panel test 27 subjects were asked to directly compare two creams. Cream 1 comprised a combination of the polyether siloxane according to reference example 4 and ceteareth-25 as coemulsifier, and cream 2 comprised exclusively ceteareth-25 as emulsifier (see formulations cream 1 and cream 2). FIG. 1 shows the result of the panel test: with regard to the spreadability and the absorption, cream 1 (invention) was very much preferred, and with regard to the care effect there was a slight preference for cream 1. The feel on the skin of cream 1 was again very much preferred to that of cream 2 (prior art). The result of this is that a clear majority of the subjects chose cream 1.

Cream 1: Invention

| | | |
|---|---|---|
| A | Polyether siloxane according to reference example 4 | 1.5% |
| | Ceteareth-25 | 1.0% |
| | Glyceryl stearate | 2.5% |
| | Stearyl alcohol | 1.5% |
| | Stearic acid | 1.0% |
| | Caprylic/Capric triglyceride | 6.0% |
| | Cetearyl ethylhexanoate | 6.5% |
| B | Glycerol | 2.0% |
| | Water | 77.5% |
| C | TEGO ® carbomer 134 (carbomer) | 0.1% |
| | Paraffinum liquidum | 0.4% |

Cream 2: Prior Art

| | | |
|---|---|---|
| A | Ceteareth-25 | 2.0% |
| | Glyceryl stearate | 2.5% |
| | Stearyl alcohol | 1.5% |
| | Stearic acid | 1.0% |
| | Caprylic/Capric triglyceride | 6.5% |
| | Cetearyl ethylhexanoate | 6.5% |
| B | Glycerol | 2.0% |
| | Water | 77.5% |
| C | TEGO ® Carbomer 134 (carbomer) | 0.1% |
| | Paraffinum liquidum | 0.4% |

Example 13

Figure 2:
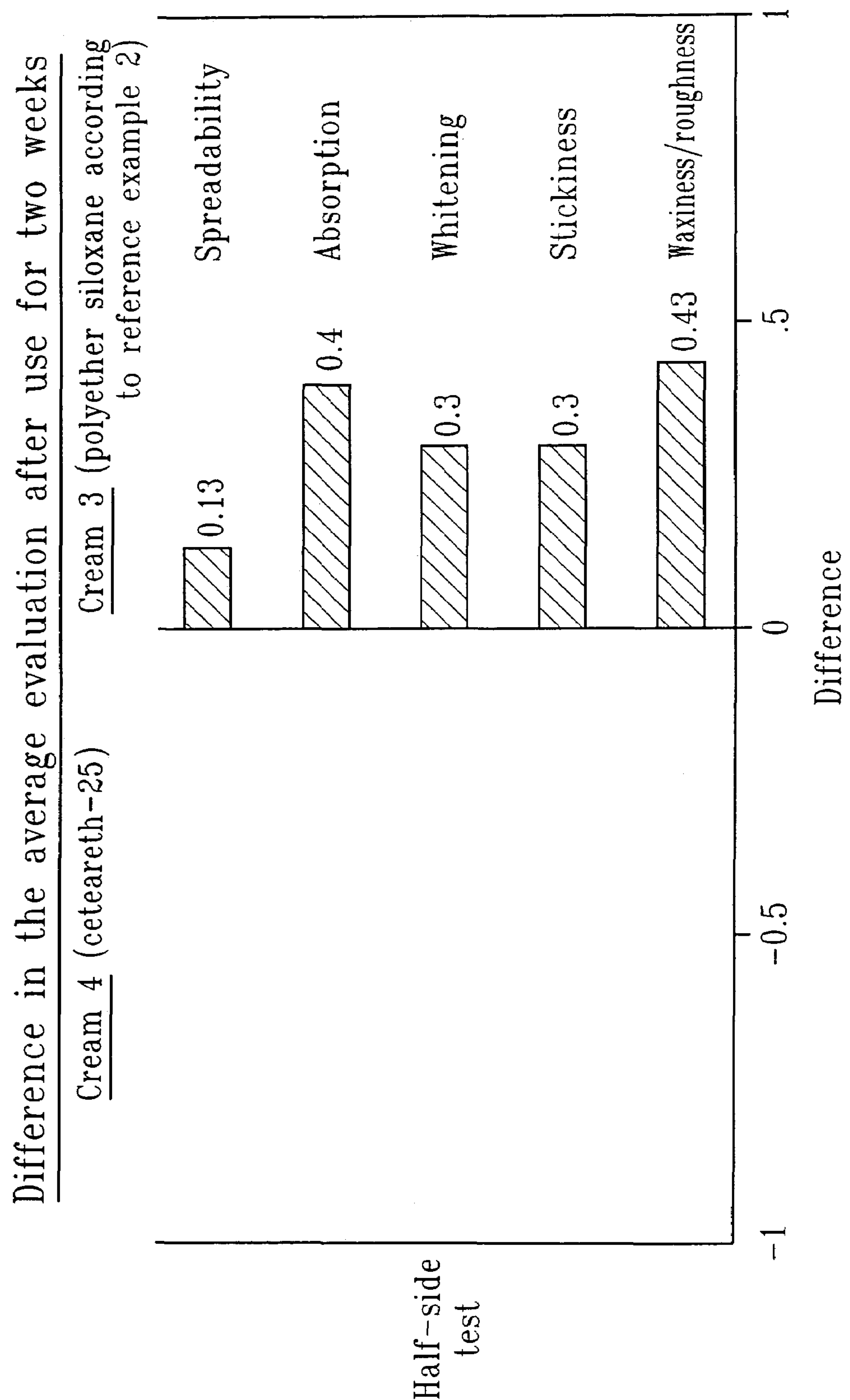
FIG. 2 shows the results of the panel test with creams 3 & 4 prepared in Example 13.

In a panel test 20 subjects were asked to directly compare two creams. Cream 3 (Invention) comprised a combination of the polyether siloxane according to reference example 2 and ceteareth-25 as coemulsifier, and cream 4 (Prior Art) comprised exclusively ceteareth-25 as emulsifier (see formulations cream 3 and cream 4). FIG. 2 shows the result of the panel test: with regard to the attributes spreadability, absorption, whitening, stickiness and waxiness/roughness, cream 3 was preferred significantly over cream 4.

Cream 3: Invention

| | | |
|---|---|---|
| A | Polyether siloxane according to reference example 2 | 1.8% |
| | Ceteareth-25 | 0.2% |
| | Glyceryl stearate | 1.5% |
| | Stearyl alcohol | 2.5% |
| | Stearic acid | 1.0% |
| | Paraffinum liquidum | 6.5% |
| | Ethylhexyl stearate | 6.5% |
| B | Glycerol | 3.0% |
| | Water | 77.0% |

Cream 4: Prior Art

| | | |
|---|---|---|
| A | Ceteareth-25 | 2.0% |
| | Glyceryl stearate | 1.5% |
| | Stearyl alcohol | 2.5% |
| | Stearic acid | 1.0% |
| | Paraffinum liquidum | 6.5% |
| | Ethylhexyl stearate | 6.5% |
| B | Glycerol | 3.0% |
| | Water | 77.0% |

Example 14

The water resistance of a sunscreen lotion containing the polyether siloxane according to reference example 1 was tested in vivo in accordance with Colipa. For this purpose, the light protection factor is determined and the measurement is repeated after wetting of the treated site. Prior to wetting, the lotion had a sun protection factor of 14, and after wetting a sun protection factor of 10. This corresponds to a water resistance of 71%. A product may be referred to as water resistant if the water resistance is at least 50%. In particular, it is to be pointed out that the formulation does not comprise ingredients which are used expressly for increasing the water resistance, such as e.g. film-forming polymers.

| | | |
|---|---|---|
| A | Polyether siloxane according to reference example 1[1)] | 1.7% |
| | ABIL ® B 8863 | 0.3% |
| | C12–15 alkyl benzoate | 3.0% |
| | Paraffinum liquidum | 3.4% |
| | 4-Methylbenzylidenecamphor | 3.0% |
| | Ethylhexyl methoxycinnamate | 2.5% |
| | Butyl methoxydibenzoylmethane | 2.0% |
| | Isoamyl p-methoxycinnamate | 2.5% |
| | Tocopheryl acetate | 0.5% |
| B | TEGO ® SMO 80 (Polysorbate 80) | 0.2% |
| | Glycerol | 2.0% |
| | EDTA | 0.1% |
| | GluCare ® S (sodium carboxymethyl betaglucan) | 0.1% |
| | Water | 75.9% |
| C | TEGO ® Carbomer 140 (carbomer) | 0.15% |
| | TEGO ® Carbomer 141 (carbomer) | 0.15% |
| | Xanthan gum | 0.1% |
| | Isopropyl palmitate | 1.6% |
| D | Sodium hydroxide (10% in water) | 0.8% |
| | Preservative, perfume | q.s. |

[1)]ABIL ® B 8863: Comb-like polyether siloxane with a proportion by weight of the polyether radicals of the total molecular mass of 76%.
Sunscreen lotion While the present invention has been particularly shown and described with respect to preferred embodiments thereof, it will be understood by those skilled in the art that the foregoing and other changes in forms and details may be made therein without departing from the spirit and scope of the present invention. It is therefore intended that the present invention not be limited to the exact forms and details but fall within the scope of the appended Claims.

What is claimed is:

1. A cosmetic or pharmaceutical oil-in-water emulsion which comprises at least one polyether siloxane of the general formula (I)

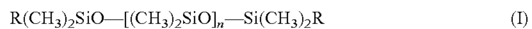

$$R(CH_3)_2SiO—[(CH_3)_2SiO]_n—Si(CH_3)_2R \quad (I)$$

where n=50 to 250

$R=—(CH_2)_m—O—(C_2H_4O)_x—(C_3H_6O)_yR^1$ m=2 to 4 x=3 to 100 y=0 to 50

$R^1$=H, $CH_3$, or $CH_2CH_3$, having a proportion by weight of the polyether radicals R of up to 45%, by weight, of the total molecular mass; and at least one stabilizer selected from the group consisting of a liquid-crystalline-structure forming hydrophilic wax, a water-swellable organopolymer, and a mixture of a liquid-crystalline-structure forming hydrophilic wax and a water swellable organopolymer, wherein said oil-in-water emulsion is free of silicone oils.

2. The cosmetic or pharmaceutical oil-in-water emulsion of claim 1 further comprising at least one coemulsifier.

3. The cosmetic or pharmaceutical oil-in-water emulsion of claim 2 wherein said at least one stabilizer is said hydrophilic wax.

4. The cosmetic or pharmaceutical oil-in-water emulsion of claim 3 wherein said hydrophilic wax is selected from the group consisting of stearyl alcohol, stearic acid, glyceryl stearate and mixtures thereof.

5. The cosmetic or pharmaceutical oil-in-water emulsion of claim 2, wherein the proportion of the polyether siloxane of the general formula (I), in the case of the presence of coemulsifiers is, based on the total amount of the emulsifiers, at least 50% by weight.

6. The cosmetic or pharmaceutical oil-in-water emulsion of claim 5 wherein the proportion of polyether siloxane is 65 to 95%, by weight.

7. The cosmetic or pharmaceutical oil-in-water emulsion of claim 2 wherein the proportion of the coemulsifier of the total amount of the emulsifiers is 5 to 49%, by weight.

8. The cosmetic or pharmaceutical oil-in-water emulsion of claim 7 wherein said proportion is from 10 to 350%, by weight.

9. The cosmetic or pharmaceutical oil-in-water emulsion of claim 1 further comprising auxiliaries and additives selected from the group consisting of UV light protecting filters, antioxidants, preservatives, insect repellents, self-tanning agents, perfume oils, dyes and active ingredients.

10. A process of preparing an oil-in-water emulsion comprising:

emulsifying a silicone oil-free oil phase in a water phase with at least one polyether siloxane of the general formula (I)

$$R(CH_3)_2SiO—[(CH_3)_2SiO]_n—Si(CH_3)_2R \quad (I)$$

where n=50 to 250

$R=—(CH_2)_m—O—(C_2H_4O)_x—(C_3H_6O)_yR^1$ m=2 to 4 x=3 to 100 y=0 to 50

$R^1$=H, $CH_3$, or $CH_2CH_3$, having a proportion by weight of the polyether radicals R of up to 45% of the total molecular mass, and at least one stabilizer selected from the group consisting of liquid-crystalline-structure forming hydrophilic waxes, water swellable organopolymers and combinations thereof to provide an emulsion.

11. The process of claim 10 wherein said oil-in-water emulsion further comprises a coemulsifier.

12. The process of claim 10 wherein said at least one stabilizer is said hydrophilic wax which is selected from the group consisting of stearyl alcohol, stearic acid, glyceryl stearate and mixtures thereof.

13. A cosmetic or pharmaceutical oil-in-water emulsion which comprises 10 weight percent or less of a monohydric alcohol; and at least one polyether siloxane of the genial formula (I)

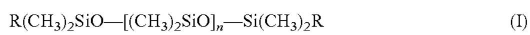

$$R(CH_3)_2SiO—[(CH_3)_2SiO]_n—Si(CH_3)_2R \quad (I)$$

where n=50 to 250

$R=—(CH_2)_m—O—(C_2H_4O)_x—(C_3H_6O)_yR^1$ m=2 to 4 x=3 to 100 y=0 to 50

$R^1$=H, $CH_3$, or $CH_2CH_3$, having a proportion by weight of the polyether radicals R of up to 45%, by weight, of the total molecular mass, and at least one stabilizer selected from the group consisting of a liquid-crystalline-structure forming hydrophilic wax, a water-swellable organopolymer, and a mixture of a liquid-crystalline-structure forming hydrophilic wax and a water swellable organopolymer, wherein said oil-in-water emulsion is free of silicone oils.

14. The cosmetic or pharmaceutical oil-in-water emulsion of claim 13 further comprising at least one coemulsifier.

15. The cosmetic or pharmaceutical oil-in-water emulsion of claim 14 wherein said at least one stabilizer is said hydrophilic wax.

16. The cosmetic or pharmaceutical oil-in-water emulsion of claim 15 wherein said hydrophilic wax is selected from the group consisting of stearyl alcohol, stearic acid, glyceryl stearate and mixtures thereof.

17. The cosmetic or pharmaceutical oil-in-water emulsion of claim 14, wherein the proportion of the polyether siloxane of the general formula (I), in the case of the presence of coemulsifiers is, based on the total amount of the emulsifiers, at least 50% by weight.

18. The cosmetic or pharmaceutical oil-in-water emulsion of claim 17 wherein the proportional of polyether siloxane is 65 to 95%, by weight.

19. The cosmetic or pharmaceutical oil-in-water emulsion of claim 14 wherein the proportion of the coemulsifier of the total amount of the emulsifiers is 5 to 49%, by weight.

* * * * *

UNITED STATES PATENT AND TRADEMARK OFFICE

CERTIFICATE OF CORRECTION

PATENT NO. : 7,074,419 B2

APPLICATION NO. : 09/777544

DATED : July 11, 2006

INVENTOR(S) : Thomas Dietz et al.

It is certified that error appears in the above-identified patent and that said Letters Patent is hereby corrected as shown below:

Column 18, Line 24, Claim 8:

"The cosmetic or pharmaceutical oil-in-water emulsion of claim 7 wherein said proportion is from 10 to 350%, by weight."

should read

Column 18, Line 24, Claim 8:

-- The cosmetic or pharmaceutical oil-in-water emulsion of claim 7 wherein said proportion is from 10 to 35%, by weight. --

Column 18, Line 61, Claim 13:

"A cosmetic or pharmaceutical oil-in-water emulsion which comprises 10 weight percent or less of a monohydric alcohol;
and at least one polyether siloxane of the genial formula (I)"

should read

Column 18, Line 61, Claim 13:

--A cosmetic or pharmaceutical oil-in-water emulsion which comprises 10 weight percent or less of a monohydric alcohol;
and at least one polyether siloxane of the general formula (I) --

Signed and Sealed this

Twenty-sixth Day of June, 2007

JON W. DUDAS

*Director of the United States Patent and Trademark Office*